United States Patent [19]

Mitra

[11] 4,396,604

[45] Aug. 2, 1983

[54] SIMETHICONE ANTACID LOZENGE

[75] Inventor: Arun K. Mitra, Olivette, Mo.

[73] Assignee: Norcliff Thayer, Inc., Tarrytown, N.Y.

[21] Appl. No.: 379,379

[22] Filed: May 17, 1982

[51] Int. Cl.³ .................. A61K 31/695; A61K 31/19; A61K 33/06; A61K 33/12; A61K 33/10; A61K 33/08

[52] U.S. Cl. .................... 424/154; 424/155; 424/156; 424/157; 424/184; 424/317

[58] Field of Search ............... 424/154, 184, 156, 157

[56] References Cited

U.S. PATENT DOCUMENTS

| | | | |
|---|---|---|---|
| 2,926,121 | 2/1960 | Hobbs et al. | 424/156 |
| 2,934,472 | 4/1960 | May | 424/184 |
| 2,951,011 | 8/1960 | Feinstone | 424/184 |
| 3,382,150 | 5/1968 | Grass et al. | 424/184 |
| 3,422,189 | 1/1969 | Rider | 424/184 |
| 3,501,571 | 5/1970 | Yen | 424/184 |
| 3,767,794 | 10/1973 | McVean et al. | 424/184 |
| 4,127,650 | 11/1978 | Buehler | 424/184 |
| 4,163,777 | 8/1979 | Mitra | 424/157 |
| 4,198,390 | 4/1980 | Rider | 424/184 |

FOREIGN PATENT DOCUMENTS

| | | | |
|---|---|---|---|
| 1129260 | 10/1968 | United Kingdom | 424/184 |
| 2033915 | 5/1980 | United Kingdom | 424/155 |

OTHER PUBLICATIONS

Handbook of Nonprescription Drugs, 5th ed., pp. 13–17.

Primary Examiner—Stanley J. Friedman
Assistant Examiner—F. Abramson

[57] ABSTRACT

Provided is a method and lozenge composition which permits antacid and simethicone to be in intimate contact while still maintaining unimpaired defoaming activity of simethicone.

12 Claims, No Drawings

ND LOZENGE

BACKGROUND OF THE INVENTION

(1) Field of the Invention

The present invention relates generally to pharmaceutical lozenges and, more particularly, to a method for making a lozenge; the lozenge containing an antacid ingredient and an antiflatulent ingredient consisting of simethicone.

(2) Prior Art

Mitra, U.S. Pat. No. 4,163,777, discloses a lozenge containing antacid. The antacid in the lozenge is slowly dissolved in the mouth, which provides a sustained release of antacid which neutralizes stomach acid over a long period of time.

According to an official F.D.A. manuscript on over-the-counter drugs, simethicone is the only product that has been held to be a safe and effective antiflatulent. It has been widely used for years by itself or in combination with antacids in liquid and tablet form.

However, it has long been known that most antacids inactivate simethicone by adsorption (study of Morton Rezak published in the Journal of Pharmaceutical Science 55:538–539, May, 1966). Some of the antacids that have marked deleterious effects on the deforming activity of simethicone are aluminum hydroxide, magnesium carbonate, bismuth subcarbonate, magnesium carbonate-aluminum hydroxide coprecipitate, and others. The antacids that have the least effect are sodium bicarbonate and sodium citrate. Antacids with a medium effect are calcium carbonate, magnesium trisilicate and magnesium hydroxide.

Many attempts have been made in the past to overcome this incompatability of simethicone and antacids in the solid dosage form and patent literature on this subject for the period 1960 to 1980 is revealing. Primarily attempts have been, one way or another, to manufacture formulations where these two ingredients are physically kept apart.

The May U.S. Pat. No. 2,934,472 and Feinstone U.S. Pat. 2,951,011 respectively, pertain to antiflatulency of simethicone and combination of simethicone with antacid.

U.S. Pat. No. 3,382,150 issued to Grass and MacDonnell describes a process of spray-drying organopolysiloxanes with gums and various other materials that result in a free-flowing particulate material with the silicone coated with gums, etc. The purpose of this invention is to supply a convenient solid form of oily organopolysiloxane so that it can be easily incorporated in a tablet.

The Rider U.S. Pat. No. 3,422,185 describes the concept of activation of organopolysiloxanes by incorporation of small amounts of silica aerogel but does not address itself to the inactivation problem with antacids.

The Yen U.S. Pat. No. 3,501,571 discloses the art of dispersing the silicone first in an adsorbent such as lactose and then making the antacid tablet as a double-layered tablet where the antacid and simethicone are separated into different layers or are mixed and made into a single layer tablet.

The U.S. Pat. No. 3,767,794 issued to McVean and Tuereck teaches to disperse up to 20% simethicone in molten sorbitol and then incorporate the powdered, solidified simethicone into antacid tablets. The solidified sorbitol physically protects the simethicone from the antacid in a tablet and hence prevents its deactivation.

U.S. Pat. No. 4,127,650 of Buehler is similar to that of McVean and Tuereck except it uses a combination of glycerol and corn syrup.

Rider U.S. Pat. No. 4,198,390 proposes to achieve the same objective by incorporating the simethicone in a nonantacid layer and separating this from the antacid layer by a third layer which is termed the barrier layer.

Today, most commerical antacid-simethicone tablets are sold as two-layered products to prevent the inactivation of simethicone in the tablet form by antacids. The first layer contains only simethicone and diluents and the second layer contains antacids and diluents but with no simethicone. The purpose of manufacturing the product in two layers is to prevent the inactivation of simethicone by the antacids through intimate contact.

However, these commercial products are not entirely successful in preventing inactivation of simethicone.

Most of the antacid-simethicone tablets currently available in the marketplace in the United States, have been tested by the inventor and found to have not only the simethicone partially deactivated but, in most cases, completely deactivated in the available products. Thus, most of these antacids did not pass the USP XX defoaming test for simethicone. Only a few of of these products, on some occasions, barely passed the test; and it can be surmised that with more shelf life these products would also fail the test.

Furthermore, at least a partial explanation of deactivation was unexpectedly discovered. While assaying the two layers of commercial products, it was discovered that approximately 90 percent of the labeled amount of simethicone was in the antacid layer and only 10 percent of the labeled amount of simethicone was in the nonantacid layer. This fact could only be explained by assuming that after the tablet was manufactured, the simethicone migrated from the antacid-free simethicone layer to the antacid layer due to the strong attractive force on the simethicone by the antacid. While it has been observed before that commercial antacid-simethicone tablets fail to pass the USP deforming test, an adequate explanation of the phenomenon was lacking.

It would be desirable to have a commercially-acceptable product which combines antacid and simethicone in one layer and which has a sustained release of both products. In the lozenge of the invention, the antacid and the simethicone are in the same layer without any deactivation of the simethicone. This lack of deactivation of simethicone, while in intimate contact with antacid, lacks an adequate explanation at this time. Studies show that in the lozenge of the present invention there is no diminution of simethicone activity even at elevated temperatures with passage of time.

SUMMARY OF THE INVENTION

A lozenge and method for making a lozenge which maintains antacid and simethicone in one layer and in intimate contact without any deactivation of simethicone is disclosed.

The method comprises using a process for making hard candy having steps including (1) cooking a candy base, (2) mixing a cooked molten candy composition, and (3) forming a hard candy lozenge; wherein antacid is placed into the candy base during or prior to the cooking step, and simethicone is placed into the candy base prior to cooking or into the cooked molten candy composition during or prior to mixing.

The lozenge of the invention comprises a hard candy composition, antacid and simethicone. Optionally, it may contain other additives known to the hard candy art.

DETAILED DESCRIPTION OF THE INVENTION

In the lozenge according to the present invention, the antacid component, or acid neutralizing substance, can be any of various nontoxic sodium, calcium, magnesium or aluminum salts used to neutralize gastric fluids. Illustrative antacids are sodium bicarbonate, sodium citrate, calcium carbonate, calcium phosphate, magnesium oxide, magnesium hydroxide, magnesium carbonate, and magnesium trisilicate. Other suitable antacids include dihydroxy aluminum sodium carbonate, dihydroxy aluminum aminoacetate and magnesium hydroxy aluminates. It is preferred that the neutralizing substance in the present dosage form be a calcium carbonate, magnesium carbonate or mixtures thereof.

Simethicone is described in The United States Pharmacopia, 20th Edition, 1980, as a mixture of fully methylated linear siloxane polymers containing repeating units of the formula $[-(CH_3)_2SiO-]_n$, stabilized with trimethylsiloxy end-blocking units of the formula $[(CH_3)_3SiO-]$, and silicon dioxide. It contains not less than 90.5% and not more than 99.0% of polydimethylsiloxane ($[-(CH_3)_2SiO-]_n$), and not less than 4.0% and not more than 7.0 percent of silicone dioxide. Dimethylpolysiloxane is sometimes referred to as polysiloxane or organopolysiloxane.

In the present invention, any known hard candy composition may be used.

Suitable hard candy compositions can be made from varying, but highly concentrated, sucrose solutions including corn syrup as a second essential ingredient. One suitable formulation, for example, includes from about 55% to about 90% by weight of sucrose solids and from about 10% to about 45% by weight of corn syrup solids dissolved in a small amount of water.

Other known hard candy compositions may utilize any suitable good testing, sweet excipient other than sucrose. These compositions may also be used in the present invention.

These other sweet excipients include dextrose and the sugar alcohols, mannitol and sorbitol. Sugar alcohols are particularly preferred for use herein because they provide lozenges which are "sugarless" and, hence, noncarcinogenic.

When the sweet excipient is an sugar alcohol, it may be necessary to add an artificial sweetner to provide a lozenge with an acceptable taste. While sorbitol is preferred, it may be substituted by or used in combination with other sugar alcohols.

The amount of sweet excipient is selected to give the lozenge a pleasantly sweet taste. For the purpose, the sweet excipient makes up 25 to 60% by weight of the lozenge, preferably from 35 to 50%.

In the practice of the present invention, the antacid powder is added to a hard candy base before it is fully cooked. In a preferred embodiment, the antacid is added to the sucrose solution which is then boiled to remove some of the water. The corn syrup is then added and the mixture heated to about 230° F. Thereafter, the partially cooked candy mass is further cooked under vacuum. As the partially cooked candy mass emerges from the precooker, it contains from about 65% to about 80% by weight solids. By the time the fully cooked candy mass is discharged from the vacuum cooker, the water content has been reduced to about 0.5% to about 2.0%, and is preferably no more than 1.0% by weight of the finished lozenge.

In a variation of the above-described method, the antacid powder is not added to the sucrose solution until it has been partially cooked or even until after the corn syrup has been added. The antacid is added, however, before the base is cooked to the hard candy stage. Otherwise, the method is as described above.

The simethicone may be added to the candy base prior to cooking or may be added to the molten cooked candy composition during or prior to cooking. It is preferred that the simethicone and, optionally, coloring, flavorants and additive is added to the candy mass when it is removed from the vacuum cooker and uniformly mixed throughout the mixture by kneading it until it is homogeneous. It is then formed into lozenges by conventional procedures. For example, the candy may be formed into a rope and converted by appropriate means into lozenges of the desired shape and size.

The amount of antacid powder incorporated into the hard candy antacid lozenges of the present invention can vary from about 10% to about 25% by weight. Preferably, it is present in an amount from about 15% to about 20% by weight. To provide an effective therapeutic dose, each lozenge should contain from about 5 meq to about 30 meq of acid neutralizing capacity.

The amount of simethicone incorporated into the hard candy lozenge of the present invention can vary from about 0.2% to about 4.0% by weight. Preferably, is is present in an amount from about 0.5% to about 2.0% by weight.

For the lozenge to be comfortably retained in the patient's mouth, it should weigh from about 2 g to about 6 g. The present invention provides a way in which an effective dose of antacid and simethicone can be incorporated in a hard candy lozenge of such a size. In addition to antacid, the lozenges may also contain suitable excipients, stabilizing and other agents.

The following examples are given by way of illustrating the invention. The amounts and ratios of sugars, sugar-alcohols, antacid ingredients and simethicone, can be easily varied by one skilled in the art.

EXAMPLE I

Add 315 lb of liquid sugar (66.7% solids) to a 600 lb capacity steam-jacketed kettle equipped with stirrer. Add with stirring 50 lb of precipitated calcium carbonate. Add under mixing 90 lb of liquid corn syrup (76.5% solids). Add 0.82 gm of F.D.&C. Blue No. 1 and 0.245 g of D.&C. Yellow No. 10. With steam, heat the above mixture to a temperature of 224° F. to 230° F. This partially cooked antacid candy composition is passed through a series of heat exchangers and comes out at the exit end as final cooked candy composition lozenge with approximately 0.5% moisture at a temperature of 305° F. to 315° F. This cooked candy composition flows in a stream to a metal trough with stirrers and is mixed with flavor and simethicone. The flow of the cooked candy composition, flavor and simethicone are so controlled that the final product has the desired amount of ingredients. In this experiment, 4 fl. oz. of peppermint oil and 14 fl. oz. of simethicone are added and mixed with 100 lb of cooked candy composition. This mixture is deposited into moving molds, cooled, ejected and sized so that each piece of lozenge weighs 3.4 gm. This 3.4 gm antacid-antiflatulent lozenge contains 0.5 gm of calcium carbonate and 30 mg of simethicone. When tested under the conditions prescribed for defoaming activity of simethicone in U.S.P. XX, it shows an endpoint of seven seconds while the upper limit is 45 seconds. This lozenge under accelerated storage conditions shows little diminution in defoaming activity.

EXAMPLE II

Exact amounts of materials and procedure were used as in Example I with the exception of substituting the 50 lb of calcium carbonate with a mixture of 37.5 lb of calcium carbonate and 12.5 lb of magnesium carbonate. The resulting lozenge was as effective as that of Example I in defoaming activity.

EXAMPLE III

The 50 lb of calcium carbonate of Example I were substituted with 50 lb of magnesium carbonate. The resulting lozenge was as effective as that of Example I in antacid and defoaming activity.

EXAMPLE IV

The 50 lb of calcium carbonate of Example I were substituted with a mixture of 37.5 lb of calcium carbonate and 12.5 lb of magnesium hydroxide. The resulting lozenge had effective antacid and defoaming activity.

EXAMPLE V

Two hundred eighty-five gm of sorbitol and 15 gm of manitol were dissolved in 90 ml of boiling water in a stainless steel beaker. To this solution was added, in order, with stirring, 25 gm of calcium carbonate and 25 gm of magnesium carbonate. This suspension was then slowly heated with stirring to a temperature of 385°–390° F. in a mineral oil bath to get rid of the water. This cooked sugarless lozenge mixture was then cooled to 150° F., when 3 gm of low volatile simethicone were carefully added with stirring. The cooked lozenge was then poured into molds so that when cooled and hardened, we obtained sugarless antacid-antiflatulent lozenges, each weighing 3.5 gm. These lozenges were effective antacids and exceptionally prompt defoaming dosage forms.

COMPARITIVE EXAMPLES

The following commercial products in the tablet form were compared to the lozenge of Examples 1, 2, 3, 4 and 5 using the defoaming test of U.S.P. XX.

The test procedure and results follow.

The defoaming test of U.S.P. XX for simethicone basically calls for a 250 ml flask with screw cap of specific dimensions, a defoaming solution containing the product with 20 mg of simethicone, 1 mg of octoxynol, and 500 ug of F.D.&C. Blue No. 1 and a wrist shaker that is shaken for 10 seconds under specified conditions. To pass the defoaming test, the solution should defoam and show a clear liquid layer in less than 45 seconds.

| Defoaming Activity of Marketed Products and Experimental Products | |
|---|---|
| Product | Defoaming Activity (seconds) |
| Gelusil M | 90 |
| Mylanta II | 40, 45, 70 90 |
| Gelusil II | 90 |
| DiGel | 90 |
| Riopan Plus | 90 |
| Experimental Product of | 7 |
| Examples 1, 2, 3, 4 and 5 | |

I claim:

1. A process for preparing an antacid/antifoaming pharmaceutical lozenge having an antacid and simethicone in intimate contact without deactivation of simethicone comprising the steps of:
   (a) melting by heat about 25% to 60% by weight a sweet excipient in water solution, said sweet excipient being selected from the group consisting of sucrose, corn syrup, dextrose, mannitol and sorbitol;
   (b) adding by mixing about 10% to 25% by weight of a pharmaceutically acceptable sodium, calcium, magnesium or aluminum antacid salt used to neutralize gastric fluids;
   (c) adding by mixing about 0.2% to 4.0% by weight simethicone to said mixture;
   (d) cooking the mixture under vacuum and reducing water content to about 0.5% to 2.0% by weight;
   (e) completing cooking by passing said mixture through a heat exchanger; and
   (f) forming said mixture into hard lozenges.

2. The process of claim 1 wherein said simethicone is added to said mixture of sweet excipient and antacid salt during the cooking step d.

3. The process of claim 1 wherein coloring and flavorants are added to said mixture along with simethicone in step c.

4. The antacid/antifoaming pharmaceutical lozenge prepared by the process of claim 1.

5. A process for preparing an antacid/antifoaming pharmaceutical lozenge having an antacid and simethicone in intimate contact without deactivation of simethicone comprising the steps of:
   (a) adding and mixing to obtain a homogeneous mixing of about 10% to 25% by weight of a pharmaceutically acceptable sodium calcium, magnesium or aluminum antacid salt used to neutralize gastric fluids to about 25% to 60% by weight of a sweet excipient selected from the group consisting of sucrose, corn syrup, dextrose, mannitol and sorbitol dissolved in water;
   (b) boiling said mixture to remove some of the water;
   (c) cooking the mixture under vacuum and reducing water content to about 0.5% to 2.0% by weight;
   (d) completing cooking by passing said mixture through a heat exchanger;
   (e) adding by kneading about 0.2% to 4.0% by weight simethicone to said mixture; and
   (f) forming said mixture into hard lozenges.

6. The antacid/antifoaming pharmaceutical lozenge prepared by the process of claim 5.

7. A process for preparing an antacid/antifoaming pharmaceutical lozenge having an antacid and simethicone in intimate contact without deactivation of simethicone comprising the steps of;
   (a) adding with mixing to obtain a homogeneous mixture of about 10% to 25% by weight of an antacid substance selected from the group consisting of sodium bicarbonate, sodium citrate, calcium carbonate, calcium phosphate, magnesium oxide, magnesium hydroxide, magnesium carbonate, magnesium trisilicate, dihydroxy aluminum sodium carbonate, dihydroxy aluminum aminoacetate and magnesium hydroxy aluminate to about 25% to 60% by weight of a sweet excipient selected from the group consisting of sucrose, corn syrup, dextrose, mannitol and sorbitol dissolved in water;

(b) boiling said mixture to remove some of the water;

(c) cooking the mixture under vacuum and reducing water content to about 0.5% to 2.0% by weight;

(d) passing said mixture through a heat exchanger at a temperature of about 350° F. to 315° F.;

(e) adding by kneading about 0.2% to 4.0% by weight simethicone to said mixture; and (f) forming said mixture into hard lozenges.

8. The process of claim 7 wherein the water content of said mixture under vacuum cooking in step c is reduced to less than 1.0% by weight of the finished lozenge.

9. The antacid/antifoaming pharmaceutical lozenge prepared by the process of claim 7.

10. A process for preparing an antacid/antifoaming pharmaceutical lozenge having an antacid and simethicone in intimate contact without deactivation of simethicone comprising the steps of:

(a) adding with stirring 15% to 20% by weight of an antacid substance selected from the group consisting of sodium bicarbonate, sodium citrate, calcium carbonate, calcium phosphate, magnesium oxide, magnesium hydroxide, magnesium carbonate, magnesium trisilicate, dihydroxy aluminum sodium carbonate, dihydroxy aluminum aminoacetate and magnesium hydroxy aluminate to 35% to 50% by weight of a liquid sugar selected from the group consisting of sucrose, corn syrup, dextrose, mannitol and sorbitol.

(b) mixing said components to obtain a homogeneous mixture;

(c) heating said mixture to a temperature of about 224° F. to 230° F.;

(d) passing said mixture through a heat exchanger at a temperature of 305° F. to 315° F. to reduce water content to about 0.5% by weight;

(e) adding with mixing about 0.5% to 2.0% by weight simethicone; and (f) forming said mixture into hard lozenges weighing about 2 to about 6 gm.

11. The process of claim 10 wherein said liquid sugar comprises about 55% to 90% by weight of sucrose solids and about 10% to 45% by weight of corn syrup solids.

12. The antacid/antifoaming pharmaceutical lozenge prepared by the process of claim 10.

* * * * *